United States Patent [19]

Schulz, Jr.

[11] Patent Number: 5,015,624

[45] Date of Patent: May 14, 1991

[54] PROCESS FOR REDUCTION OF ORGANOHALOSILANES

[75] Inventor: William J. Schulz, Jr., Midland, Mich.

[73] Assignee: Dow Corning Corporation, Midland, Mich.

[21] Appl. No.: 516,599

[22] Filed: Apr. 30, 1990

[51] Int. Cl.$^5$ ............................................. C07F 7/08
[52] U.S. Cl. .................................................. 556/474
[58] Field of Search ........................................ 556/474

[56] References Cited

U.S. PATENT DOCUMENTS

| | | | |
|---|---|---|---|
| 2,567,972 | 9/1951 | Schlesinger et al. | 556/474 X |
| 2,857,414 | 10/1958 | Schmidt et al. | 556/474 |
| 3,043,857 | 7/1962 | Jenkner | 556/474 X |
| 3,100,788 | 10/1963 | Jenkner | 556/474 |
| 3,496,206 | 2/1970 | Berger | 556/474 |
| 3,499,020 | 3/1970 | Robinson | 556/474 |
| 3,607,897 | 9/1971 | Michael | 556/474 |
| 3,627,803 | 12/1971 | Michael | 556/474 |
| 3,704,261 | 11/1972 | Berger et al. | 556/474 X |
| 4,542,005 | 9/1985 | Tetsuya et al. | 556/474 X |

*Primary Examiner*—Paul F. Shaver
*Attorney, Agent, or Firm*—William F. Boley

[57] ABSTRACT

The present invention is a process for reducing the number of halogens on organohalosilanes and volatile organohalopolysilanes, while preventing unwanted reactions. The process takes advantage of the high susceptibility of the silicon-halogen bond to chemical reduction by an alkylaluminum hydride. This susceptibility allows the halogen to be quickly removed from the organohalosilane, forming reduced product, before less favorable reactions can occur. The reduced product is immediately removed from the reaction mixture by vacuum distillation, preventing further reactions. The process may be used to remove one or more, or all, of the halogens from organohalosilanes and volatile organohalopolysilanes.

20 Claims, No Drawings

PROCESS FOR REDUCTION OF ORGANOHALOSILANES

BACKGROUND OF INVENTION

The present invention is a process for reducing organohalosilanes and volatile organohalopolysilanes. The process takes advantage of the high susceptibility of silicon-halogen bonds to alkylaluminum hydride reducing agents. The high susceptibility of the silicon-halogen bond to chemical reduction allows a process to be run where the resultant reduced product can be removed from a reaction mixture before additional or less favorable reactions can occur.

The process comprises forming a mixture of the halosilane, to be reduced, and a liquid alkylaluminum hydride reducing agent. The organohalosilane is only contacted with the alkylaluminum hydride long enough for the reactive silicon-halogen bond to be reduced. Temperature and pressure conditions of the process are controlled such that the boiling reduced product is caused to immediately vaporize from the mixture without undergoing further reaction.

The described process can be run to control the number of halogen atoms remaining on silicon. That is, both fully and partially reduced silanes can be produced. The process can be run as a one-step process requiring no additional separation steps to recover the reduced silanes.

The silicon-halogen bond is known to be a highly reactive bond that can be rapidly reduced to the corresponding silicon-hydrogen species in the presence of reducing agents. Generally, the more halogen atoms present on a particular silicon atom, the greater the reactivity of the silicon-halogen bond. For example, the order of reactivity for the silicon-chlorine bond is $RSiCl_3 > R_2SiCl_2 > R_3SiCl$ where R is a hydrocarbon group.

Jenkner, U.S. Pat. No. 3,100,788, issued Aug. 13, 1963, teaches the reduction of organohalosilanes by reaction with hydrogen in the presence of alkali metals, or with alkali hydrides. The reaction is carried out at elevated temperatures in the range of 50° C. to 400° C. and pressures of 1 atm to 350 atm or more. One of the benefits Jenkner claims for this process is that very few compounds of Si-Si structure are produced.

Berger, U.S. Pat. No. 3,496,206, issued Feb. 17, 1970, describes a process whereby an alkali metal hydride is used in combination with an alkylaluminum halide, to effect the reduction of organohalosilanes. The preferred process employed a substantially inert organic solvent and a temperature between 100° C. to 130° C. The reduced product was subsequently distilled.

Robinson, U.S. Pat. No. 3,499,020, issued Mar. 3, 1970, teaches the reduction of halogen containing silanes with dialkylaluminum hydrides in the presence of an inert solvent and an ether. The process was ran under closed conditions and the reduced product subsequently isolated. Robinson teaches that care must be taken in the reduction of compounds containing unsaturated linkages to maintain the temperature substantially below 100° C. in order to prevent the occurrence of addition reactions.

Schulz, Co-Pending U.S. application Ser. No. 07/531,616, filed 6/1/90, now U.S. Pat. No. 4,973,723, describes a process in which halosilacycloalkanes are reduced with an alkylaluminum hydride to produce silacycloalkanes. In the described process, the silacycloalkane is immediately vaporized from the mixture to prevent further reaction with the alkylaluminum hydride.

None of the cited art recognizes that the uniquely reactive nature of the silicon-halogen bond present in organohalosilanes and organohalopolysilanes makes possible a process in which the bond can be reduced and the reduced product removed from the mixture before other, less favorable, processes can occur.

BRIEF SUMMARY OF INVENTION

The present invention is a process for reducing organohalosilanes and volatile organohalopolysilanes. The process comprises forming a mixture of the silane to be reduced and a liquid alkylaluminum hydride reducing agent. The organohalosilane is only contacted with the alkylaluminum hydride long enough for the reactive silicon-halogen bond to be reduced. Temperature and pressure conditions of the process are controlled such that the lower boiling, reduced, product is caused to immediately vaporize from the mixture without undergoing further reaction.

The described process minimizes undesirable reactions of the organosilanes and organopolysilanes as well as allowing recovery of partially reduced species. Typically, the process can be run as a one-step process requiring no additional separation steps for recovery of the reduced species.

DESCRIPTION OF INVENTION

Described, is a process for the preparation of reduced organosilanes and volatile reduced organopolysilanes. The reduced organosilanes that can be prepared by the present process are of the formula:

$$R_nSiH_aX_{4-n-a};$$

where each R is independently selected from the group consisting of alkyl, cycloalkyl, alkenyl, aryl, aralkyl, halogenated alkyl, and halogenated aryl radicals; n=1 or 2; a=1, 2, or 3; n+a=3 or 4; and X is a halogen.

The volatile reduced organopolysilanes that can be prepared by the present described process are of the formula:

$$R_dSi_yH_eX_{2y+2-d-e};$$

where R is independently selected from the group consisting of alkyl, cycloalkyl, alkenyl, aryl, aralkyl, halogenated alkyl, and halogenated aryl radicals; y is an integer of 2 through 6; d is an integer of 1 through 2y+1; e is an integer of 1 through 2y+1; d+e is an integer of 2 through 2y+2; and X is a halogen.

The process for preparing the reduced organosilanes and volatile reduced organopolysilanes comprises:
(A) forming a mixture comprising an organohalosilane of formula:

$$R_nSiH_bX_{4-n-b};$$

where R, n, and X are as previously described; b=0, 1, or 2; and n+b=1, 2, or 3;
or a volatile organohalopolysilane of formula:

$$R_dSi_yH_fX_{2y+2-d-f};$$

where R, X, d, and y are as previously described; f is an integer of 0 through 2y; and d+f is an integer of 1 through 2y+1;
and a liquid alkylaluminum hydride of formula $$R'_c AlH_{3-c};$$

where R' is an alkyl group of one to 10 carbon atoms and c=1 or 2;

(B) effecting reaction of the organohalosilane or volatile organohalopolysilane with the alkylaluminum hydride; and (C) maintaining mixture temperature and vessel pressure sufficient to effect immediate vaporization of reduced organosilanes or reduced volatile organopolysilanes from the mixture.

The present invention is a process for reducing the halogen content of an organohalosilane or an organohalopolysilane. The process takes advantage of the relative ease with which silicon-halogen bonds can be reduced by an alkylaluminum hydride. The halogen containing organo- silane or organopolysilane is contacted with the alkylaluminum hydride only long enough for the reactive silicon-halogen bond to be reduced. Temperature and pressure conditions of the process are maintained such that the reduced product is immediately vaporized from the mixture before other, less energetically favorable, reactions can occur. The described process may be used to remove one or more, or all of the halogens from the organohalosilane or organohalopolysilane. When organohalosilanes are the material to be reduced, it is preferred that one or two hydrocarbon radicals be present on the silicon atom. Although organohalosilanes with three hydrocarbon radicals substituted on the silicon atom will work in the described process, the silicon-halogen bond is stable enough that, in most cases, no significant processing advantage is gained by the instant described process. An exception to this general rule is when the silicon atom has highly reactive hydrocarbon radicals attached to it, for example, an alkylsilacyclobutane.

The described process reduces the halogen content of an organohalosilane or a volatile organohalopolysilane. The organic substituent (R) can be, for example, alkyl radicals such as methyl, ethyl, n-propyl, isopropyl, n-butyl, secbutyl, tert-butyl, amyl, hexyl, heptyl octyl, dodecyl, pentadecyl, octadecyl; cycloalkyl radicals such as cyclobutyl, cyclopentyl, cyclohexyl, cycloheptyl, and cyclooctyl; alkenyl radicals such as vinyl, 1-propenyl, and allyl; aryl radicals such as phenyl, tolyl, and xylyl; aralkyl radicals such as benzyl, $\beta$-phenylethyl, $\beta$phenylpropyl, and gamma-tolylpropyl; halogenated alkyl radicals such as chloromethyl, 3-chloropropyl, bromooctadecyl, 3,3,3-trifluoropropyl, 3,3,3,-trichloropropyl and perfluoroethyl; and halogenated aryl radicals such as chlorophenyl, dichlorophenyl, fluorophenyl, difluorophenyl, bromophenyl, and iodophenyl. Any combination of the above organic radicals on silicon is considered within the scope of the claimed invention. Preferred, is when the organic substituent, R, is independently chosen from the group comprising methyl, vinyl, phenyl, and 3,3,3-trifluoropropyl radicals.

The halogen substituent can be independently chosen bromo, chloro, iodo, and fluoro radicals. Preferred is when the halogen is a chloro radical.

The organohalosilane can be, for example, dimethyldichlorosilane, diphenyldichlorosilane, methylvinyldichlorosilane, methylphenyldichlorosilane, diallyldichlorosilane, 3,3,3-trifluoropropylmethyldichlorosilane, bis-3,3,3-trifluoropropyldichlorosilane, dimethyldifluorosilane, dimethylfluorobromosilane methyltrichlorosilane, ethyltrichlorosilane, npropyltrichlorosilane, n-butyltrichlorosilane, phenyltrichlorosilane, phenyltrifluorosilane, vinyltrichlorosilane cyclopentyltrichlorosilane, cyclobutyltrichlorosilane, allyltrichlorosilane, phenyldichlorofluorosilane, phenyltribromosilane, methyldichlorosilane, ethyldichlorosilane, propyldichlorosilane, allyldichlorosilane, phenyldichlorosilane, and 3,3,3-trifluoropropyldichlorosilane.

The preferred volatile organohalopolysilanes are diand trisilanes, where the organic substituents, R, are independently chosen from a group consisting of methyl, ethyl, vinyl, phenyl, and 3,3,3-trifluoropropyl radicals. The term "volatile organohalopolysilanes" refers to those materials which will vaporize within the temperature and pressure parameters defined for the present process i.e. a maximum mixture temperature less than 200° C. and minimum vessel pressure of $1 \times 10^{-4}$. The volatile organohalopolysilane can be, for example, pentamethylchlorodisilane, pentamethylbromodisilane, pentamethylfluorodisilane, tetramethyldichlorodisilane, 1,1,2,2-tetramethyl1,2-dichlorosilane, 1,1,2,2-tetramethyl-1,2-dibromodisilane, 1,1,2,2-tetramethyl-1,2-difluorodisilane, methylpentachlorodisilane, methylchlorodisilane, diethyl-tetrachlorodisilane, and 1,1,2,2,3,3-hexamethyl-1,3-dichlorotrisilane.

The organohalosilanes and organohalopolysilanes are reduced by contact with an alkylaluminum hydride. The alkylaluminum hydride can be, for example, ethylaluminum hydride, isobutylaluminum hydride, diethylaluminum hydride, diisopropylaluminum hydride, diisobutylaluminum hydride, or diisoamylaluminum hydride. The preferred alkylaluminum hydride is diisobutylaluminum hydride.

In a preferred embodiment of the instant invention, a sealed vessel capable of maintaining a pressure differential relative to normal atmospheric pressure, while adding feed materials and removing product, is employed. Due to the pyrophoric nature of the alkylaluminum hydride, the vessel is flushed with an inert gas, for example, argon, helium, or nitrogen prior to addition of the alkylaluminum hydride. A quantity of alkylaluminum hydride is then added to the vessel. Alternatively, the alkylaluminum hydride can be diluted with an inert solvent, for example hexane, heptane, toluene, benzene, or tetrahydrofuran. When a 15 to 25 percent solution of the alkylaluminum hydride in solvent is used, it is recommended, but not necessary, to flush the reaction apparatus with an inert gas. However, use of a solvent can create additional separation steps. Therefore, it is preferred sufficient alkylaluminum hydride be added to the vessel undiluted.

It is preferred that the alkylaluminum hydride be added to the reaction apparatus to provide a slight molar excess of available hydrogen, i.e. Al-H, in relation to the amount of halogen to be removed from the organohalosilane or organohalopolysilane. By slight excess, is meant up to 10 percent molar excess of hydrogen. Greater relative amounts of alkylaluminum hydride may be used, but will result in incomplete consumption of the alkylaluminum hydride. Likewise, lessor amount of the alkylaluminum hydride can be employed, but will result in incomplete reduction of the organohalosilane or organohalopolysilane. The alkylaluminum halide formed as a result of the described process may be recycled to other processes, for example, as a catalyst for olefin polymerization.

The organohalosilanes and organohalopolysilanes to be reduced by the described process are typically volatile under the described process conditions. Therefore, it is important that the mixture be formed in such a manner as to ensure adequate contact between the organohalosilane or organohalopolysilane and the liquid alkylaluminum hydride. Actual contact conditions will depend upon both contact time required to reduce the desired silicon-halogen bonds as well as the volatility of the reactant organohalosilane or organohalopolysilane. In addition, due to the exothermic nature of the reduction reaction, it is important that the rate of addition of the organohalosilane to the alkylaluminum halide be controlled. Actual addition rates will depend upon factors such as reactivity of the reactants, reactor vessel size, volume of alkylaluminum halide employed, and facilities for control of the mixture temperature.

The preferred procedure for forming the mixture is to deliver the organohalosilane or organohalopolysilane beneath the surface of the alkylaluminum hydride. The organohalosilane or organohalopolysilane is delivered at a depth beneath the surface of the alkylaluminum hydride that allows for adequate residence time within the alkylaluminum hydride for reduction to occur before the organohalosilane or organohalopolysilane can exit the mixture as a vapor. The organohalosilane or organohalopolysilane may be delivered beneath the surface of the alkylaluminum hydride, for example, by such means as a tube inserted beneath the surface of the alkylaluminum hydride or an entrance port in the wall of the vessel and below the surface of the alkylaluminum hydride.

Effecting reaction of the organohalosilane or organohalopolysilane with the alkylaluminum hydride encompasses, as previously described, achieving adequate contact time between the alkylaluminum hydride and the organohalosilane or organohalopolysilane for reduction to occur. In addition to the actual physical method of forming the mixture, a combination of mixture temperature and vessel pressure can be used to effect reaction of the organohalosilane or organohalopolysilane with the alkylaluminum halide.

Any mixture temperature above the freezing temperature of the alkylaluminum halide and less than 200° C. may be used. A preferred temperature range for the process is 0° C. to 100° C. A vessel pressure of about $1 \times 10^{-4}$ atms to 3 atms may be used for the process. A preferred process pressure range is $1 \times 10^{-3}$ atms to one atm. Preferred is a combination of temperature and pressure sufficient for reduction of the organohalosilane within the mixture and which allows the reduced products to be immediately vaporized from the mixture. A mixing means, such as a magnetic stirrer and stirring bar, or the equivalent, may be used to improve contact of the alkylaluminum hydride with the organohalosilane or organohalopolysilane and assist in effecting the reaction.

A combination of mixture temperature and vessel pressure conditions are used to effect immediate vaporization of reduced organosilanes or reduced organopolysilanes from the mixture. By "immediate vaporization" is meant the reduced organosilanes or organopolysilanes are removed from the mixture before they have an opportunity to undergo additional chemical reaction. The temperature and pressure conditions which may be employed are as previously described for effecting reaction of the organohalosilane or organohalopolysilane with the alkylaluminum hydride. It is preferred that the product vapors be removed from contact with the reaction vessel as they are formed.

The removed organosilane and organohalopolysilane product vapors may be used as feed to another process or may be collected by means such as a cold trap and stored for future use. The reduced products may be collected or used without additional separation or purification steps, in which case the process is run as a one-step process. Alternatively the reduced products may undergo additional separation or purification steps.

Products which may be produced by the described process are reduced organosilanes, which includes both organosilanes and partially reduced organohalosilanes, with reduced halogen content. The reduced organosilanes can be for example: dimethylsilane, diphenylsilane, methylvinylsilane, methylphenylsilane, diallylsilane, bis-(3,3,3-trifluoropropyl)silane, methylsilane, phenylsilane, ethylsilane, n-propylsilane, n-butylsilane, vinylsilane, cyclopentylsilane, cyclobutylsilane, allylsilane, and 3,3,3-trifluoropropylmethylsilane. The partially reduced organohalosilanes can be, for example, dimethylchlorosilane, diphenylchlorosilane, methyvinylchlorosilane, methylphenylchlorosilane, diallylchlorosilane, bis-(3,3,3-trifluoropropyl)chlorosilane, dimethylfluorosilane, methylchlorosilane, propylchlorosilane, allylchlorosilane, phenylchlorosilane, and 3,3,3-trifluoropropylchlorosilane.

Products which may be produced by the described process include both non-halogen containing organopolysilanes and partially reduced organohalopolysilanes with a reduced halogen content. The organopolysilane can be, for example, pentamethyldisilane, tetramethyldisilane, methyldisilane, 1,1,2,2,3,3-hexamethyltrisilane, and 1,1-diethyldisilane.

The partially reduced organohalopolysilane can be, for example, tetramethylchlorosilane, methytetrachlorodisilane, methyltrichlorodisilane, methyldichlorodisilane, and 1,1-diethyl-2,2-dichlorodisilane.

So that those skilled in the art may better understand and appreciate the instant invention, the following examples are presented. These examples are presented to be illustrative and are not to be construed as limiting the claims as delineated herein.

Examples. Selected organohalosilanes and organohalopolysilanes as described in Table 1 were reduced by diisobutylaluminum hydride (DIBAH).

An apparatus for vacuum distillation of reduced silanes immediately upon their formation was assembled. A three necked roundbottom flask containing a magnetic stir bar served as a reaction vessel. The lower portion of the reaction vessel was enclosed in a heating mantle. One neck of the reaction vessel was equipped with a thermometer. A second neck of the reaction vessel served as an outlet port for product. The outlet port was connected in series to a reflux condenser, a stopcock, a cold trap, and a vacuum source. The third neck of the reaction vessel was fitted with a rubber septum through which was passed a 0.30 mm i.d. teflon tube that passed to the bottom of the reaction vessel. This teflon tube was used to feed organohalosilanes and organohalopolysilanes to the reaction vessel as feedstocks. The teflon tube external to the reaction vessel was connected in series with a stopcock and then passed through a rubber septum into a 10 ml flask that served as a reservoir for the feedstock. The entire apparatus as described was pressure tight so as to allow a vacuum to be maintained.

The process was ran by first blanketing the reaction vessel with argon and then charging the reaction vessel with 18 ml (0.101 mole) neat DIBAH. The system was stirred and evacuated to the pressure as detailed in Table 1. The reaction vessel was then warmed to the specified temperature. The feed material reservoir was charged with feedstock sufficient to yield 0.092 moles of chloride. The stopcock situated in the teflon tube between the feed reservoir and reaction vessel was opened to allow a slow addition of the feed material to the DIBAH; the flow rate was adjusted such that the reaction did not become violent. Generally, addition was complete in about 20 minutes. After, the addition of the feed material was completed, the system was allowed to stir at the reaction temperature and pressure for an additional 15 minutes. During the entire procedure, vapors were allowed to exit to the cold trap, where they were collected for subsequent analysis. After completion of the reaction, the system was filled with argon and the contents of cold trap removed and identified.

The results are presented in Table 1. The pressure and temperature conditions under which each halosilane was reacted is given. The "%Yield" is the mole percent of reduced product recovered in relation to the number of moles of halosilane added to the reaction vessel. "%Yield" is given for both the fully reduced product as well as for partially reduced product. The term "%Rec." refers to the mole percent of the feedstock recovered unchanged.

TABLE 1

| Halosilane | Press. (mm Hg) | °C. | % Yield Fully Reduced | % Yield Part. Reduced | % Rec. |
|---|---|---|---|---|---|
| Reduction of Organohalosilanes and Organohalopolysilanes With Diisobutylaluminum Hydride. | | | | | |
| $(CH_3)_3SiCl$ | 760 | 55 | 69 | N/A | 31 |
| $PhSiCl_3$ | 1 | 70 | 99 | 0 | Trace |
| $(CH_2=CHCH_2)_2SiCl_2$ | 1 | 80 | 70 | 12 | 7 |
| $MeViSiCl_2$ | 1 | 25 | 0 | 1 | 98 |
| $CF_3CH_2CH_2SiMeCl_2$ | 1 | 43 | 4 | 11 | 85 |
| $Me_3SiSiMeCl_2$ | 1 | 50 | 70 | 9 | 4 |

The examples partially illustrate the scope of organohalosilanes and organohalopolysilanes which can be reduced either partially or wholly by the described process.

What is claimed is:

1. A process for preparation of reduced organosilanes of the formula $$R_nSiH_aX_{4-n-a};$$

where R is independently selected from the group consisting of alkyl, cycloalkyl, alkenyl, aryl, aralkyl, halogenated alkyl, and halogenated aryl radicals; n = 1, 2, or 3; a = 1, 2, or 3; n+a = 3 or 4; and X is a halogen; the process comprising:
  (A) forming a mixture comprising an organohalosilane of formula $$R_nSiH_bX_{4-n-b};$$

where R, n, and X are as previously described; b = 0, 1, or 2; and n+b = 1, 2, or 3; and an alkylaluminum hydride of formula $$R'_cAlH_{3-c};$$

where R' is an alkyl group of one to 10 carbon atoms and c = 1 or 2; in a vessel;
  (B) effecting reaction of the organohalosilane with the alkylaluminum hydride; and
  (C) maintaining mixture temperature and vessel pressure sufficient to effect immediate vaporization of reduced organosilanes from the mixture.

2. A process according to claim 1, where the alkylaluminum hydride is diisobutylaluminum hydride.

3. A process according to claim 1, where the forming of a mixture is effected by delivering the organohalosilane beneath the surface of the alkylaluminum hydride at a controlled rate.

4. A process according to claim 1, where the mixture temperature is in the range of 0° C. to 100° C.

5. A process according to claim 1, where the vessel pressure is in the range of $1 \times 10^{-3}$ atm to 1 atm.

6. A process according to claim 1, where the reduced organosilane vapors are removed from contact with the mixture as the vapors are formed.

7. A process according to claim 1, where the process is run as a one-step process.

8. A process according to claim 2, where R is independently selected from the group consisting of methyl, vinyl, phenyl, and 3,3,3-trifluoropropyl radicals and X is a chloro radical.

9. A process according to claim 2, where the organohalosilane is phenyltrichlorosilane.

10. A process according to claim 2, where the organohalosilane is diallyldichlorosilane.

11. A process according to claim 2, where the organohalosilane is methylvinyldichlorosilane.

12. A process according to claim 2, where the organohalosilane is 3,3,3-trichloropropylmethydichlorosilane.

13. A process for preparation of volatile reduced organopolysilanes of the formula $$R_dSi_yH_eX_{2y+2-d-e};$$

where R is independently selected from the group consisting of alkyl, cycloalkyl, alkenyl, aryl, aralkyl, halogenated alkyl, and halogenated aryl radicals; y is an integer of 2 through 6; d is an integer of 1 through 2y+1; e is an integer of 1 through 2y+1; d+e is an integer of 2 through 2y+2; and X is a halogen the process comprising:
  (A) forming a mixture comprising a volatile organohalopolysilane of formula $$R_dSi_yH_fX_{2y+2-d-f};$$

where X, d, and y are as previously described; f is integer of 0 through $2y+1$; and $d+f$ is an integer of 1 through $2y$;

and an alkylaluminum hydride of formula $$R'_c AlH_{3-c};$$

where R' is an alkyl group of one to 10 carbon atoms and $c=1$ or 2; in a vessel;

(B) effecting reaction of the volatile organohalopolysilane with the alkylaluminum hydride; and (C) maintaining mixture temperature and vessel pressure sufficient to effect immediate vaporization of volatile reduced organopolysilanes from the mixture.

14. A process according to claim 13, where the alkylaluminum hydride is diisobutylaluminum hydride.

15. A process according to claim 13, where the forming of a mixture is effected by delivering the organohalosilane beneath the surface of the alkylaluminum hydride at a controlled rate.

16. A process according to claim 13, where the mixture temperature is in the range of 0° C. to 100° C.

17. A process according to claim 1, where the vessel pressure is in the range of $1 \times 10^{-3}$ atm to 1 atm.

18. A process according to claim 13, where the reduced organosilane vapors are removed from contact with the mixture as the vapors are formed.

19. A process according to claim 13, where the process is run as a one-step process.

20. A process according to claim 14, where R is independently selected from the group consisting of methyl, vinyl, phenyl, and 3,3,3-trifluoropropyl radicals and X is a chloro radical.

* * * * *